United States Patent [19]

Sivik et al.

[11] Patent Number: 5,520,835
[45] Date of Patent: May 28, 1996

[54] AUTOMATIC DISHWASHING COMPOSITIONS COMPRISING MULTIQUATERNARY BLEACH ACTIVATORS

[75] Inventors: Mark R. Sivik, Fairfield; Lucille F. Taylor, Middletown; James C. T. R. Burckett-St. Laurent, Cincinnati, all of Ohio

[73] Assignee: The Procter & Gamble Company, Cincinnati, Ohio

[21] Appl. No.: 438,126

[22] Filed: May 8, 1995

Related U.S. Application Data

[63] Continuation-in-part of Ser. No. 298,904, Aug. 31, 1994.

[51] Int. Cl.$^6$ .................. C11D 3/395; C11D 7/54; C07C 101/02
[52] U.S. Cl. .................. 252/102; 252/95; 252/99; 252/174.12; 252/174.21; 252/186.27; 252/186.38; 560/155
[58] Field of Search .................. 252/95, 99, 102, 252/174.12, 174.21, 186.27, 186.38; 560/155

[56] References Cited

U.S. PATENT DOCUMENTS

| | | | |
|---|---|---|---|
| 3,650,749 | 3/1972 | Willems et al. | 96/66 |
| 3,959,461 | 5/1976 | Bailey et al. | 424/70 |
| 4,026,708 | 5/1977 | Vanassche et al. | 96/95 |
| 4,283,301 | 8/1981 | Diehl | 252/102 |
| 4,397,757 | 8/1983 | Bright et al. . | |
| 4,536,314 | 8/1985 | Hardy et al. | 252/102 |
| 4,539,130 | 9/1985 | Thompson et al. | 252/94 |
| 4,675,131 | 6/1987 | Walraevens et al. | 260/404 |
| 4,681,592 | 7/1987 | Hardy et al. | 8/111 |
| 4,751,015 | 6/1988 | Humphreys et al. | 252/99 |
| 4,818,426 | 4/1989 | Humphreys et al. | 252/99 |
| 4,853,143 | 8/1989 | Hardy et al. | 252/102 |
| 4,904,406 | 2/1990 | Darwent et al. | 252/102 |
| 4,933,103 | 6/1990 | Aoyagi et al. | 252/186.38 |
| 4,988,451 | 1/1991 | Nunn et al. | 252/95 |
| 5,041,546 | 8/1991 | Venturello et al. | 540/484 |
| 5,093,022 | 3/1992 | Sotoya et al. | 252/102 |
| 5,106,528 | 4/1992 | Francis et al. | 252/186.38 |
| 5,220,051 | 6/1993 | Sotoya et al. | 260/142 |
| 5,234,616 | 8/1993 | Mitchell et al. | 252/102 |
| 5,245,075 | 9/1993 | Venturello et al. | 560/302 |
| 5,259,981 | 11/1993 | Chapple et al. | 252/95 |
| 5,268,003 | 12/1993 | Coope et al. | 8/111 |
| 5,269,962 | 12/1993 | Brodbeck et al. | 252/186.25 |
| 5,399,746 | 3/1995 | Steiger et al. | 560/251 |

FOREIGN PATENT DOCUMENTS

| | | | |
|---|---|---|---|
| 0068547 | 1/1983 | European Pat. Off. | C11D 3/39 |
| 0106584 | 4/1984 | European Pat. Off. | C11D 3/39 |
| 0408131B1 | 1/1991 | European Pat. Off. | C11D 3/39 |
| 0540090A3 | 5/1993 | European Pat. Off. | C11D 17/00 |
| 0552812 | 7/1993 | European Pat. Off. | C07C 229/12 |
| 02011545A2 | 1/1990 | Japan | C07C 229/12 |
| 3-234796 | 2/1990 | Japan | C11D 3/39 |
| 836988 | 6/1960 | United Kingdom . | |
| 1206359 | 9/1970 | United Kingdom . | |

OTHER PUBLICATIONS

Pillersdorf and Katzhendler, Israel J. Chem. 18, 1979, 330–338.
Kirk Othmer's Encyclopedia of Chemical Tech., 4th Ed., 1992, John Wiley & Sons, vol. 4, pp. 271–300, "Bleaching Agents (Survey)".
CA 80:28403.
CA 81:107348.
CA 114:145871.
CA 114:209601.
CA 114:231055.
CA 114:231056.
CA 115:73973.
CA 116:214155.
CA 114:166810.
CA 119(18):183399e.
CA 120:253366.

*Primary Examiner*—Linda Skaling Therkorn
*Assistant Examiner*—Gregory R. Delcotto
*Attorney, Agent, or Firm*—M. D. Jones; B. M. Bolam; K. W. Zerby

[57] ABSTRACT

Improved detergent compositions, especially granular automatic dishwashing detergents, comprising multiquaternary bleach activators are provided. The bleach activators contain multiple quaternary nitrogen groups, preferably at least three such groups and preferably have at least one quaternary nitrogen group in the peracid-forming portion of the bleach activator as well as at least one quaternary nitrogen group in the leaving-group portion.

19 Claims, No Drawings

AUTOMATIC DISHWASHING COMPOSITIONS COMPRISING MULTIQUATERNARY BLEACH ACTIVATORS

RELATED APPLICATION

This invention is a continuation-in-part of commonly assigned copending U.S. patent application Ser. No. 08/298,904, filed Aug. 31, 1994.

FIELD OF THE INVENTION

The present invention is in the field of detergents with bleach, especially automatic dishwashing detergent compositions, ADD's, useful in domestic machine dishwashing. The detergents comprise oxygen bleach and multiquaternary bleach activators.

BACKGROUND OF THE INVENTION

Automatic dishwashing is a demanding field. Specialized detergent formulations are required to deliver efficient and effective sanitization and cleansing of dishware. The cleaning task includes both stain removal and tough food cleaning. Automatic dishwashing has some unique constraints as compared to fabric laundering. Spotlessness and lack of film on glasses and silverware is particularly important. In many laundering operations, in contrast, there is a tolerance for deposition, onto the substrate being cleaned, of substances which may be greasy, oily, soapy or lubricious. Such substances are often fabric softeners or fatty acid salts.

Automatic dishwashing or "machine dishwashing" as it is sometimes called also has significant differences as compared with hand dishwashing. In the latter operation, typical product formulations rely mainly on high-foaming detersive surfactants. Many such products use high-foaming quaternary ammonium surfactants. The consumer finds foam or lather to be very desirable in hand-dishwashing.

In modern automatic dishwashing formulations, tough food cleaning performance is essential. This is commonly accomplished by detersive enzymes. Alkalis are also used, but may be highly corrosive, especially at high levels. Stain removal is especially sought after by the consumer. This includes removal of stains deposited by hot beverages such as tea, coffee or the like. Stain removal is commonly accomplished by a variety of bleaches.

Several aspects of automatic dishwashing detergent compositions are markedly different from laundry compositions. For example, special nonionic surfactant types are needed owing to the very low tolerance for foam production in domestic spray-arm dishwashers. Builder systems tend to include significantly different silicates from those commonly used in laundry compositions. On the other hand, automatic dishwashing detergents, laundry detergents and other detergents such as hard surface cleaners may have features in common—for example, bleaching forms of such detergents desirably comprise cost-effective bleach systems.

Owing to the enzyme-deactivating nature of some of the most chemically effective bleaches, especially hypochlorite bleaches, compromise detergent formulations have often been provided. This includes formulations in which a relatively mild and enzyme-compatible hydrogen peroxide source, such as sodium perborate, is combined with the enzymes; optionally with tetraacetylethylenediamine (TAED) as a bleach activator.

Various efforts have been made to improve the efficacy of bleach activators and hundreds of such activators have been described in the literature; however, at present, only TAED appears to be commercially available in an ADD. Reasons for the lack of commercially successful improvements may include an emphasis on laundry improvements not easily adaptable for automatic dishwashing. Bleach activators may, for example, yield unacceptably depositing, foam-forming or malodorous peracids, none of which are acceptable for automatic dishwashing, especially in a spray-action domestic dishwasher. Unfortunately, there has been little teaching in the art as to which of the now so numerous bleach activators would be problem-free in the unique automatic dishwashing context. Other possible explanations for the lack of success of new bleach activators in automatic dishwashing is that they may simply be too costly or mass-inefficient.

The disclosure of many bleach activators in the context of laundry formulations includes the suggestion that quaternary-substituted versions of such activators may be of a depositing nature and have desirable fabric conditioning properties. See, for example, U.S. Pat. No. 4,751,015 at col. 3, lines 22-27. In light of this teaching and in view of the conventionally recognized need to minimize deposition tendencies of ingredients in automatic dishwashing, the automatic dishwashing detergent formulator would be inclined to avoid such bleach activators. This patent as well as EP 408,131 are illustrative of disclosures of bleach activators which may include chemical groups which may be cationic and/or which may form peroxycarbonic acids when perhydrolyzed.

Another quaternary substituted bleach activator is disclosed in EP 120,591 A1 published Mar. 10, 1984. The bleach activator has the structure RC(O)L wherein RC(O) is a particular acyl moiety and L is a leaving-group. It is disclosed that a quaternary nitrogen group can be included in L. Another similar disclosure is found in U.S. Pat. No. 4,681,592: see col. 10, line 29.

Additionally, EP 427,224 A1 and U.S. Pat. No. 5,220,051 describe laundry detergent compositions comprising polycationic compounds of the formula:

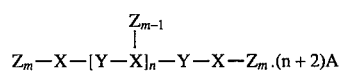

in which X is assertedly a "cation", Y is an alkylene, Z is a specific noncharged carbonyl-containing group and A is an anionic group. Based on the further illustrations in the disclosure, X is understood to be a cationic or quaternary nitrogen-containing moiety covalently incorporated into the structure. Moieties in the positions indicated by X appear to be the only quaternary nitrogen in these compounds.

Bleach activators have even been described which comprise a cationic moiety on each side of a perhydrolyzable acyl moiety. See, for example, U.S. Pat. No. 5,093,022, formula (I) at col. 1, line 50 with the substituent Y shown at col. 2, lines 40–45; and JP 02011545 A2 which describes the following bisquaternary compounds as textile bleaches and softeners:

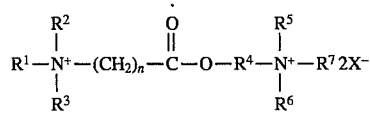

wherein $R^1$ and $R^7$ are $C_1$–$C_{22}$ alkyl; $R^2$, $R^3$, $R^5$ and $R^6$ are $C_1$–$C_5$ alkyl, hydroxyethyl or hydroxypropyl; $R^4$ is $C_2$–$C_3$ alkylene; n is from 1 to 5 and X is an anion.

Compounds of interest for hair cream rinse formulations, have a different kind of bisquaternary structure:

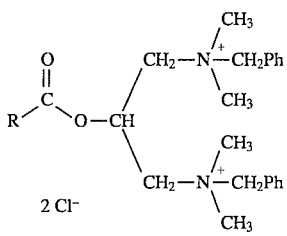

wherein R is a saturated normal alkyl group of at least 11 carbon atoms and Ph is phenyl. These are described in U.S. Pat. No. 3,959,461. Similar compounds, such as the 1,3-bis-trimethylammonium isopropyl esters of octanoic and decanoic acids, have been incorporated into laundry detergents as bleach activators. See U.S. Pat. No. 5,399,746. Such compounds, it has now surprisingly been discovered, are less effective and have certain disadvantages when used for bleach activation in automatic dishwashing detergents when compared to the bleach activators of this invention.

Whatever the bleach activators hitherto described for fabric laundering, it is not immediately evident which to select in order to improve automatic dishwashing detergents. Moreover, whatever the disclosures of the art, there remains a need for improved bleaching detergents, especially for automatic dishwashing purposes; likewise, there is an ongoing need for new, improved bleach activators.

It is therefore an object herein to provide improved detergent compositions, especially automatic dishwashing detergents, comprising multiquaternary bleach activators, especially certain multiquaternary bleach activators having specific structures disclosed hereinafter, preferably combined with a conventional hydrogen peroxide source such as sodium perborate. The detergents preferably have compact nonphosphate granular form and desirably include water-soluble silicates, low-foaming nonionic detersive surfactants particularly adapted for automatic dishwashing use, detersive enzymes, and other automatic dishwashing compatible ingredients, all formulated to deliver uncompromised levels of cleaning and stain removal without undesirable deposition on dishware, e.g., as measured by spotting/filming; and without odor- or foaming-deficiencies. Other objects include the provision of improved bleach activators for detergents, especially those designed for automatic dishwashing.

BACKGROUND ART

The above-referenced U.S. Pat. No. 4,751,015, EP 408, 131, and EP 120,591 A1 and U.S. Pat. No. 4,681,592 describe bleach activators which can include a cationic or quaternary nitrogen group. EP 427,224 A1 and U.S. Pat. No. 5,220,051, as noted, describe laundry detergent compositions comprising polycationic bleach activators. U.S. Pat. Nos. 3,959,461, 5,399,746 and JP 02011545 A2 describe diquaternary compounds, as noted. See also Pillersdorf and Katzhendler, Israel J. Chem. 18, 1979, 330–338 and Kirk Othmer's Encyclopedia of Chemical Technology, 4th. Ed., 1992, John Wiley & Sons, Vol. 4, ppg. 271–300, "Bleaching Agents (Survey)" which reviews bleaches including peroxycarboxylic acids. U.S. Pat. No. 4,260,529 discloses certain unusual cationic surfactants which assertedly may be useful bleach activators.

Other known quaternary substituted bleach activators are illustrated in U.S. Pat. Nos. 4,933,103; 4,539,130; 4,283, 301; GB 1,382,594; U.S. Pat. Nos. 4,818,426; 5,093,022; 4,904,406; EP 552,812; and EP 540,090 A2; U.S. Pat. Nos. 4,988,451; 5,268,003; 5,071,584; 5,041,546; EP 316,809; EP 68,547; EP 106,584; U.S. Pat. Nos. 4,818,426; 5,106, 528; 5,234,616; GB 836,988; JP Laid-Open 6- 655,598; EP 369,511; EP 475,511; EP 475,512; EP 475,513; JP Laid-Open 3-234- 796; EP 507,475; U.S. Pat. Nos. 4,853,143; 5,259,981; and the following Chemical Abstracts: CA 119(18):183399e; CA 81:107348; CA 80:28403; CA 120:253366; CA 116:214155; CA 115:73973; CA 114:231056; CA 114:231055; CA 114:209601; CA114:166810 and CA 114:145871. All relate to various bleach activators or peracids. U.S. Pat. No. 5,047,577 describes compounds such as dodecyldimethyl 2-acetyloxyethylammonium bromide as bleach activators. U.S. Pat. No. 4,675,131 describes quaternary ammonium salts as bleach activators. U.S. Pat. Nos. 4,026,708 and 3,650,749 describe quaternary compounds in photo processing.

SUMMARY OF THE INVENTION

It has now unexpectedly been discovered that detergent compositions, especially automatic dishwashing detergent compositions having compact, granular, nonphosphated, chlorine-free form, are significantly improved by the inclusion of specific multiquaternary bleach activators.

Accordingly the invention encompasses a detergent composition comprising an effective amount of a bleach activator having three or more quaternary nitrogen groups, wherein said bleach activator comprises a peracid-forming portion and a leaving-group portion; and wherein said peracid-forming portion comprises at least one quaternary nitrogen group, preferably from 1 to 2 quaternary nitrogen groups; and further, said leaving-group portion comprises at least one quaternary nitrogen group, preferably from 1 to 4 quaternary nitrogen groups. In general, a detergent including the identified, selected bleach activator can be formulated as a laundry detergent, hard surface cleaner, automatic dishwashing detergent, bleach additive, rinse aid, or the like; however, the preferred embodiments are automatic dishwashing detergents. These may have any convenient physical form including granules, powders, liquids, pouches, tablets, gels, pastilles, pastes and the like. Terms such as "effective amount" are defined in the detailed description hereinafter.

Typical preferred detergent compositions incorporate bleach activator comprising from three to six of said quaternary nitrogen groups in total, more preferably, from three to four such groups. In general, these are distributed between the peracid-forming portion and the leaving-group portion, as taught supra.

In general, the bleach activator may comprise more than one peracid-forming moiety within the peracid-forming portion and may comprise more than one leaving-group moiety within the leaving-group portion. However, in a preferred embodiment, the detergent composition has the form of an automatic dishwashing detergent, the bleach activator comprises a single peracid-forming moiety and a single leaving-group moiety, and said moieites are covalently connected. Thus, automatic dishwashing detergent compositions herein include those wherein said bleach activator is a salt comprising a cation having the structure:

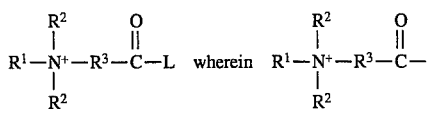 wherein

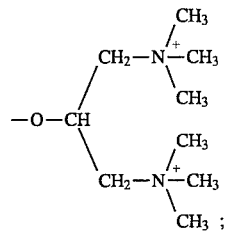

is said peracid-forming moiety and L is said leaving-group moiety; L comprises from two to five, preferably from two to three of said quaternary nitrogen groups; for example in a preferred embodiment, L is:

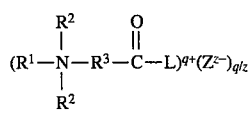

$R^1$ is $C_1$–$C_{12}$ hydrocarbyl, more preferably $C_1$–$C_6$ hydrocarbyl, more preferably still $C_1$–$C_3$ alkyl; any $R^2$ is independently selected from $C_1$–$C_4$ alkyl, $C_1$–$C_4$ hydroxyalkyl and benzyl, more preferably $C_1$–$C_4$ alkyl and benzyl, more preferably still $C_1$–$C_4$ alkyl; and $R^3$ is selected from the group consisting of $C_1$–$C_{10}$ hydrocarbyl and $R^5T$ wherein $R^5$ is $C_1$–$C_{10}$ hydrocarbyl and T is selected from NH, $NR^6$ wherein $R^6$ is $C_1$–$C_4$ hydrocarbyl, and O. Preferably, $R^3$ is $C_2$–$C_6$ hydrocarbyl, more preferably $R^3$ is $C_2$–$C_6$ alkylene. The symbol — terminating the peracid-forming moiety and L depicted supra is a connecting valence, not methyl.

In more detail, such compositions can comprise (a) an effective amount of a source of hydrogen peroxide and (b) an effective amount of a bleach activator selected from:

$$(R^1-\underset{\underset{R^2}{|}}{\overset{\overset{R^2}{|}}{N}}-R^3-\overset{\overset{O}{\|}}{C}-L)^{q+}(Z^{z-})_{q/z}$$

In these bleach activators, $R^1$, $R^2$, $R^3$ and L are identical with those defined supra; q is from 3 to 6, more preferably from 3 to 4; and Z represents one or more compatible anions having charge z– as illustrated by one or more members selected from the group consisting of bromide, chloride, phosphates, isethionate, carboxylates, polycarboxylates, methanesulfonate, ethanesulfonate, benzenesulfonate, p-toluenesulfonate, cumenesulfonate, xylenesulfonate, naphthalene sulfonate, methyl sulfate, octyl sulfate, and mixtures thereof. Preferably, in the ADD composition there will also be present a low-foaming nonionic surfactant, detersive enzyme and other adjuncts, as further detailed hereinafter. In the above, the term "hydrocarbyl" generally includes any common noncharged hydrocarbon chain-containing fragment, such as alkyl, aryl, alkylene, alkaryl or aralkyl optionally including one or more ether oxygen atoms such as may be found in an alkyl-end-capped polyoxyalkylene moiety, though ester oxygen atoms, amides and the like are not specifically excluded from this fragment of the bleach activator molecule, especially when they are perhydrolysis resistant under detergent conditions.

The present invention also encompasses automatic dishwashing detergent wash baths. Such baths are typically aqueous solutions or dispersions of the detergent and, at least upon preparation from detergent and water and before the consumption of ingredients during a wash cycle, comprise an effective amount of the above-illustrated bleach activator salt or the peracid derived therefrom by its reaction with alkaline hydrogen peroxide. Also encompassed are detergent solutions, especially low-foaming automatic dishwashing detergent solutions, comprising peracids and leaving-groups formed from the present bleach activators.

The invention includes novel bleach activators such as those identified in the hereinabove-described detergent compositions. Highly preferred bleach activators for automatic dishwashing include:

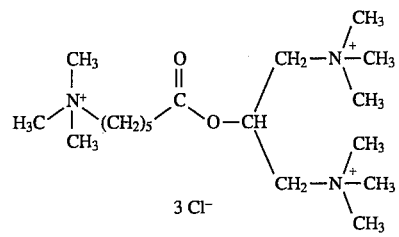

and the corresponding salts wherein $CH_3SO_4^-$ or other compatible anions replace chloride. The above bleach activator can more compactly be represented by the following abbreviation:

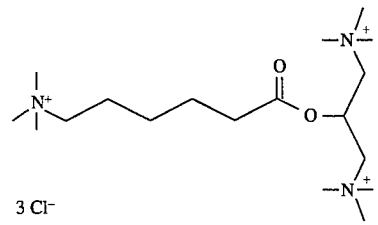

which is one commonly used by organic chemists.

All percentages and proportions herein are by weight, and all references cited are hereby incorporated by reference, unless otherwise specifically indicated.

DETAILED DESCRIPTION OF THE INVENTION

Definitions—The present detergent compositions comprise an "effective amount" or a "stain removal-improving amount" of a particularly defined bleach activator. An "effective amount" or "stain removal-improving amount" of a bleach activator is any amount capable of measurably improving stain removal (especially of tea stains) from the substrate, i.e., soiled fabric or soiled dishware, when it is washed by the consumer in the presence of alkali and sodium perborate or sodium percarbonate. In general, this amount may vary quite widely.

It is known in the art that bleach activators will "perhydrolyze" in the presence of hydrogen peroxide to form a "peracid". For example, a bleach activator of the art having the form RC(O)L, wherein RC(O) is an acyl moiety and L is a leaving-group, will react with hydrogen peroxide or a hydrogen peroxide source, such as sodium percarbonate or perborate, to form a "peracid", i.e., a percarboxylic acid RC(O)OOH or its anion, with the loss of a leaving group, L, or its conjugate acid LH. The reaction is termed "perhydrolysis". More generally the terms "peracid" and "peroxyacid" are sometimes used interchangeably in the art and are equivalent terms herein. Types of peracids are nonlimitedly illustrated by peroxyimidic acids, peroxycarbonic acids and peroxycarboxylic acids; more preferably, peroxycarbonic acids and peroxycarboxylic acids.

In general, the term "leaving group" is defined in standard texts, such as "Advanced Organic Chemistry", J. March, 4th Ed., Wiley, 1992, p 205.

The terms "portion" and "moiety" are used with particular meanings herein. Specifically, a "moiety" relates to a number of directly covalently connected atoms forming part of a molecule whereas a "portion" is used to identify a number of molecular fragments which have something in common but are not necessarily directly covalently connected. Thus, the polymeric compound:

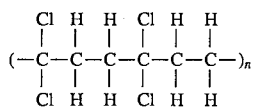

consists of a halogen portion and a non-halogen portion. The non-halogen portion consists of two $CH_2CH_2$ moieties.

A "peracid-forming portion" of a bleach activator is that individual moiety or sum of moieties of the bleach activator molecule which will form peracid entities when the bleach activator undergoes perhydrolysis. Thus, a "peracid-forming portion" will contain at least one moiety which will perhydroyze.

A "leaving group-portion" of a bleach activator is that individual moiety or sum of moieties of the bleach activator molecule which will form a leaving group or leaving groups when the molecule undergoes perhydrolysis. Thus, a leaving group-portion will separate from the peracid-forming portion of the bleach activator upon perhydrolysis of the bleach activator.

A bleach activator molecule, then, typically comprises a peracid-forming portion, a leaving-group portion and, when it has an overall charge, compatible anions or cations will be present.

Consider the case of a conventional bleach activator having the formula:

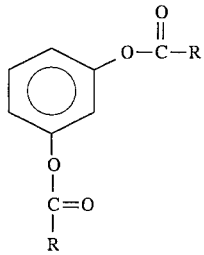

wherein both RC(O) moieties react with hydrogen peroxide, forming two moles of peracid RC(O)OOH per mole of the bleach activator. According to the present definition, this bleach activator comprises a peracid-forming portion which consists of two peracid-forming moieties, RC(O)—; and one leaving-group portion, $C_6H_4O_2$.

A "quaternary nitrogen group" herein is any simple nitrogen-containing moiety of the form:

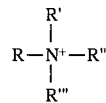

wherein R—R''' represent any acyclic, cyclic or fused substituents, preferably all being nonhydrogen substituents.

Multiquaternary Bleach Activators

The bleach activators useful in the detergent compositions of this invention comprise a peracid-forming portion and a leaving-group portion. Further, the peracid-forming portion comprises at least one quaternary nitrogen group, preferably from 1 to 2 quaternary nitrogens; the leaving-group portion comprises at least one quaternary nitrogen group, preferably from 1 to 4 quaternary nitrogen groups. Most preferably, and especially for automatic dishwashing detergent compositions, the bleach activator will comprise a single peracid-forming moiety covalently connected to a single leaving-group moiety.

Bleach activators useful in accordance with the invention are further nonlimitingly illustrated by any of the following compounds:

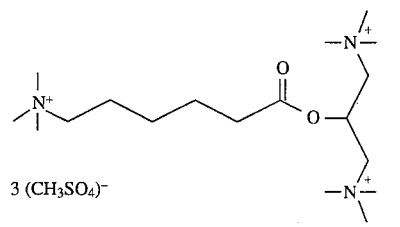

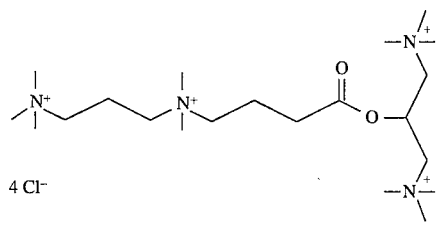

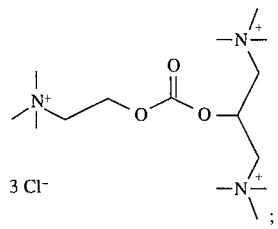

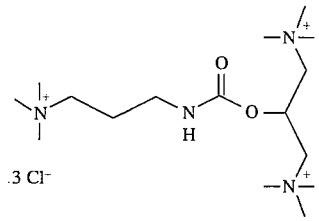

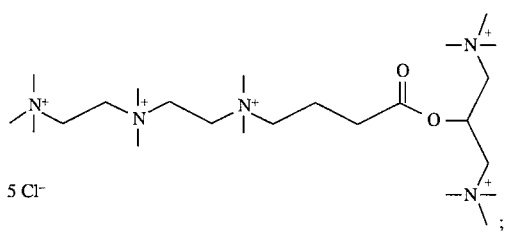

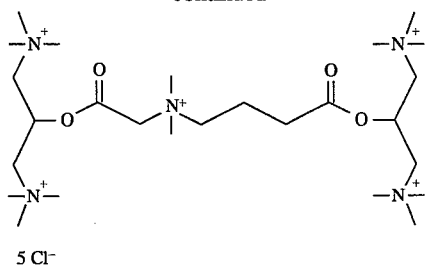

5 Cl⁻

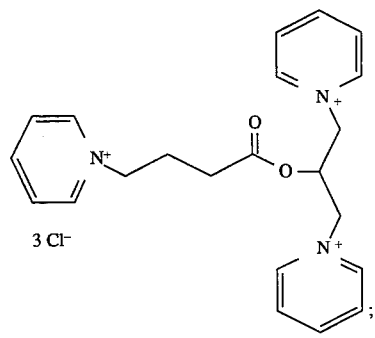

3 Cl⁻

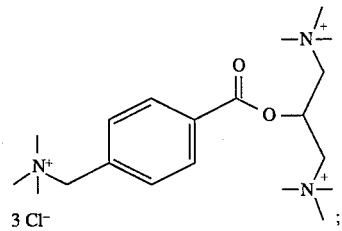

3 Cl⁻

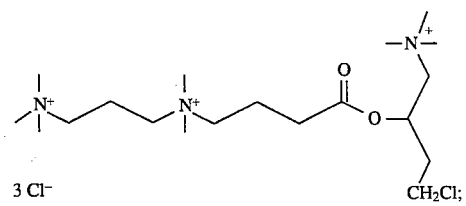

3 Cl⁻

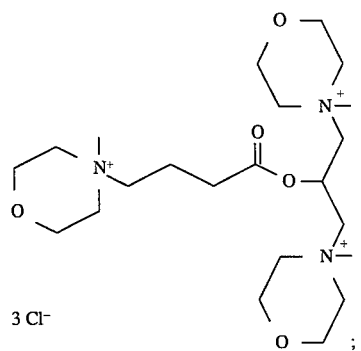

3 Cl⁻

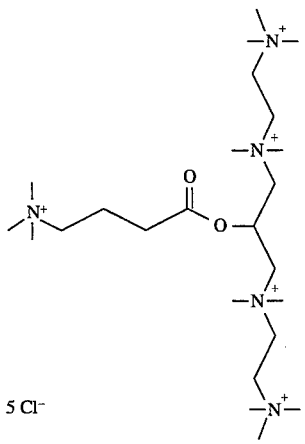

5 Cl⁻

In each of the above compounds a — symbol indicates a methyl group; though one or more methyl group can be replaced by alternate $R^2$ groups such as benzyl and the anions illustrated can be replaced by any other combination of compatible anions as taught hereinafter.

In more detail, preferred multiquaternary bleach activators suitable for use in the present compositions can comprise a cation having the structure:

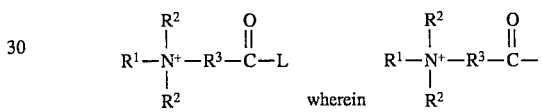

wherein is said peracid-forming moiety and L is said leaving-group moiety.

In the multiquaternary bleach activator cation (or the salt taken as a whole):

$R^1$ is $C_1$–$C_{12}$ hydrocarbyl, more preferably $C_1$–$C_6$ hydrocarbyl, most preferably $C_1$–$C_3$ alkyl;

$R^2$ is independently selected from $C_1$–$C_4$ alkyl, $C_1$–$C_4$ hydroxyalkyl and benzyl; more preferably $R^2$ is selected from $C_1$–$C_4$ alkyl and benzyl; more preferably still, $R^2$ is selected from $C_1$–$C_4$ alkyl;

$R^3$ is selected from the group consisting of $C_1$–$C_{10}$ hydrocarbyl and $R^5T$; more preferably, $R^3$ is $C_2$–$C_6$ alkylene;

$R^5$, when present, is $C_1$–$C_{10}$ hydrocarbyl; more preferably $R^5$ is $C_1$–$C_4$ hydrocarbyl; more preferably still, $R^5$ is $C_1$–$C_4$ alkylene;

T is selected from NH, $NR^6$ and O;

$R^6$ is $C_1$–$C_4$ hydrocarbyl, more preferably $C_1$–$C_4$ alkyl.

The instant multiquaternary bleach activator therefore includes structures such as:

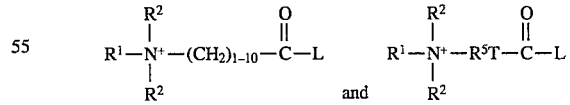

wherein T is NH, NR$^6$ or O.

In highly preferred embodiments, the multiquaternary bleach activator is substantially free from linear hydrocarbon chains having more than 6 carbon atoms. Without being bound by any particular theory of operation, the combination of particularly positioned quaternary nitrogen groups and relatively short, hydrophilic hydrocarbon chains is believed to to particularly desirable for automatic dishwashing purposes.

Leaving-Groups

In general, the multiquaternary bleach activators herein have leaving-group L comprising from two to five, preferably from two to three quaternary nitrogen groups; for example in a preferred embodiment, L is:

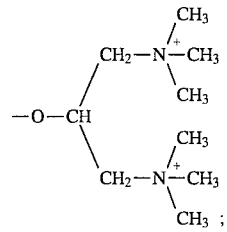

this L contains two preferred quaternary nitrogen groups, —N$^+$(CH$_3$)$_3$.

More generally, preferred leaving-groups, L, herein include those having the following formula:

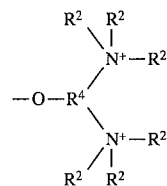

wherein R$^4$ is alkylene.
Preferably, R$^4$ is

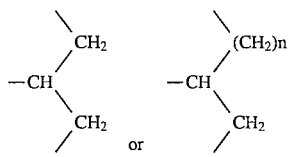

wherein n is from 1 to 4, and R$^2$ is C$_1$–C$_4$ alkyl, C$_1$–C$_4$ hydroxyalkyl or benzyl. In these fragments, a — indicates an open valence.

Further examples of highly preferred leaving-groups include

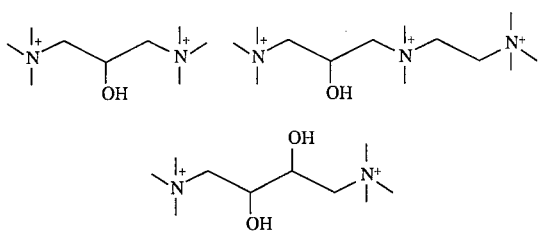

wherein a — indicates a methyl group.

Whereas the invention encompasses detergent compositions, especially ADD compositions, comprising any of the above-identified multiquaternary bleach activators, also encompassed in the invention herein are any of the bleach activators themselves, as already illustrated. Highly preferred multiquaternary bleach activators, especially for use in the automatic dishwashing compositions herein, comprise a cation having any of the following structures, together with compatible anions:

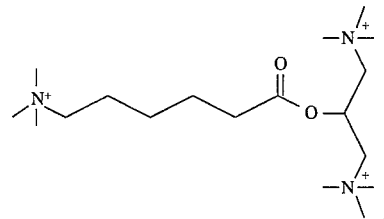

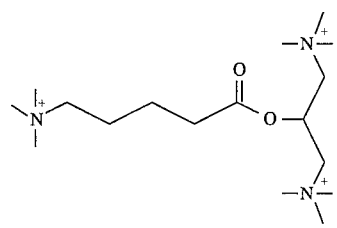

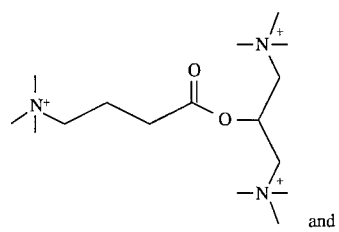

and

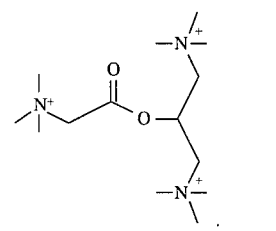

In highly preferred embodiments, the bleach activators of this invention consist essentially of a salt of the cation and one or more compatible anions.

Compatible anions—Compositions of this invention preferably comprise charge-balancing compatible anions, "counter-ions" or "counter-anions", identified as "Z" in the bleach activators herein. An index, "z", refers to the number of such counter-ions in the bleach activator. In general, the counter-anions may be monovalent, divalent, trivalent or polyvalent. Available anions such as bromide, chloride or phosphates may be used, though they may be other than preferred for one or another reason, such as bleach reactivity or phosphorus content. Examples of compatible anions include those selected from the group consisting of sulfate, isethionate, alkanesulfonate, alkyl sulfate, aryl sulfonate, alkaryl sulfonate, carboxylates, polycarboxylates, and mixtures thereof. Additionally, preferred anions include the sulfonates selected from the group consisting of methanesulfonate, ethanesulfonate, benzenesulfonate, p-toluenesulfonate, cumenesulfonate, xylenesulfonate, naphthalene sulfonate and mixtures thereof. Especially preferred of these sulfonates are those which contain aryl. Examples of alkyl sulfates include methyl sulfate and octyl sulfate. A single bleach activator compound may comprise mixtures of any of the compatible anions in charge balancing amounts, e.g., a mixture of sulfonates to chlorides may comprise a ratio of from about 1:10 to about 10:1, preferably from about 1:10 to about 5:1. As another example, a bleach activator having an overall charge of +3 in the cation may comprise a mixture of $(CH_3SO_4)^-$ and $2Cl^-$ as the compatible anions. Polycarboxylate anions suitable herein are nonlimitingly illustrated by terephthalate, polyacrylate, polymaleate, poly (acrylate-comaleate), or similar polycarboxylates; preferably such polycarboxylates have low molecular weights, e.g., 1,000–4,500. Suitable monocarboxylates are further illustrated by benzoate, naphthoate, p-toluate, and similar hard-water precipitation-resistant monocarboxylates.

Automatic Dishwashing Detergent Compositions

ADD compositions of the present invention comprise a source of oxygen bleach, preferably a source of hydrogen peroxide and a particularly selected multiquaternary bleach activator. The source of hydrogen peroxide is typically any common hydrogen-peroxide releasing salt, such as sodium perborate or sodium percarbonate. In the preferred embodiments, additional ingredients such as water-soluble silicates (useful to provide alkalinity and assist in controlling corrosion), low-foaming nonionic surfactants (especially useful in automatic dishwashing to control spotting/filming), dispersant polymers (which modify and inhibit crystal growth of calcium and/or magnesium salts), chelants (which control transition metals), builders such as titrate (which help control calcium and/or magnesium and may assist buffering action), alkalis (to adjust pH), and detersive enzymes (to assist with tough food cleaning, especially of starchy and proteinaceous soils) are present. Additional bleach-improving materials such as bleach catalysts or conventional bleach activators such as TAED may be added, provided that any such bleach-improving materials are delivered in such a manner as to be compatible with the purposes of the present invention. The present detergent compositions may, moreover, comprise one or more processing aids, fillers, perfumes, conventional enzyme particle-making materials including enzyme cores or "nonpareils", as well as pigments, and the like. In general, materials used for the production of ADD compositions herein are preferably checked for compatibility with spotting/filming on glassware. Test methods for spotting/filming are generally described in the automatic dishwashing detergent literature, including DIN test methods. Certain oily materials, especially at longer chain lengths, and insoluble materials such as clays, as well as long-chain fatty acids or soaps which form soap scum are preferably limited or excluded from the instant compositions.

Amounts of the essential ingredients can vary within wide ranges, however preferred automatic dishwashing detergent compositions herein (which have a 1% aqueous solution pH of from about 7 to about 12, more preferably from about 9 to about 12) are those wherein there is present: from about 0.1% to about 70%, preferably from about 0.5% to about 30%, of a source of hydrogen peroxide; from about 0.1% to about 30%, preferably from about 0.1% to about 10%, of the essential multiquaternary bleach activator; from about 0.1% to about 40%, preferably from about 0.1% to about 20%, of a water-soluble silicate; and from about 0.1% to about 20%, preferably from about 0.1% to about 10%, of a low-foaming nonionic surfactant. Such fully-formulated embodiments typically further comprise from about 0.1% to about 15% of a polymeric dispersant, from about 0.01% to about 10% of a chelant, and from about 0.0001% to about 10% of a detersive enzyme though further additional or adjunct ingredients may be present.

Additionally, the detergent compositions herein may further comprise a conventional bleach-improving compound, preferably selected from the group consisting of conventional bleach activators; transition metal beach catalysts; diacyl peroxides, and mixtures thereof.

Moreover the automatic dishwashing detergent compositions herein are optionally, but preferably, substantially free from chlorine bleach, calcium-precipitatable fatty acids, and phosphorus builders.

Hydrogen Peroxide Source—Hydrogen peroxide sources are illustrated in detail in the hereinabove incorporated Kirk Othmer review on Bleaching and include the various forms of sodium perborate and sodium percarbonate, including various coated, encapsulated and modified forms. An "effective amount" of a source of hydrogen peroxide is any amount capable of measurably improving stain removal (especially of tea stains) from the soiled substrate, especially dishware, compared to a hydrogen peroxide source-free composition when the soiled substrate is washed by the consumer in a in the presence of alkali.

More generally a source of hydrogen peroxide herein is any convenient compound or mixture which under consumer use conditions provides an effective amount of hydrogen peroxide. Levels may vary widely and are usually in the range from about 0.1% to about 70%, more typically from about 0.5% to about 30%, by weight of the ADD compositions herein.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Sodium perborate monohydrate and sodium percarbonate are particularly preferred. Mixtures of any convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

While effective bleaching compositions herein may comprise only the identified bleach activators and a source of hydrogen peroxide, fully-formulated ADD compositions typically will also comprise other adjunct ingredients to improve or modify performance.

Water-Soluble Silicates—The present automatic dishwashing detergent compositions may further comprise a water-soluble silicate. Water-soluble silicates herein are any silicates which are soluble to the extent that they do not adversely affect spotting/filming characteristics of the ADD composition. Typical levels are in the range from about 1% to about 15%, more preferably from about 3% to about 10% of the composition.

Examples of silicates are sodium metasilicate and, more generally, the alkali metal silicates, particularly those having a $SiO_2$:$Na_2O$ ratio in the range 1.6:1 to 3.2:1; and layered silicates, such as the layered sodium silicates described in U.S. Pat. No. 4,664,839, issued May 12, 1987 to H. P. Rieck. Na SKS-6® is a crystalline layered silicate marketed by Hoechst (commonly abbreviated herein as "SKS-6"). Unlike zeolite builders, Na SKS-6 and other water-soluble silicates useful herein do not contain aluminum. Na SKS-6 is the $\delta$-$Na_2SiO_5$ form of layered silicate and can be prepared by methods such as those described in German DE-A-3,417, 649 and DE-A-3,742,043. Na SKS-6 is a preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used. Various other layered silicates from Hoechst include Na SKS-5, Na SKS-7 and Na SKS-11, as the $\alpha$-, $\beta$- and $\gamma$- forms. Other silicates may also be useful, such as for example magnesium silicate, which can serve as a crispening agent in granular formulations, as a stabilizing agent for oxygen bleaches, and as a component of suds control systems.

Silicates particularly useful in automatic dishwashing (ADD) applications include granular hydrous 2-ratio silicates such as BRITESIL® H20 from PQ Corp., and the commonly sourced BRITESIL® H24. Such silicates may be helpful for anticorrosion effects as well as the provision of moderate alkalinity. Liquid grades of various silicates can be used when the ADD composition has liquid form. Within safe limits, sodium metasilicate or sodium hydroxide alone or in combination with other silicates may be used in an ADD context to boost wash pH to a desired level.

Low-Foaming Nonionic Surfactant—Surfactants are useful in Automatic Dishwashing to assist cleaning, help defoam food soil foams, especially from proteins, improve water-sheeting action (especially from glass), improve quick-drying action and help control spotting/filming. They are desirably included in the present compositions at levels of from about 0.1% to about 20%. Bleach-stable surfactants, and especially low foaming nonionic surfactants (LFNIs) are preferred. These are suitably at levels of from 0.1% to about 10%, preferably from about 0.25% to about 4% of the composition. LFNIs are illustrated by nonionic alkoxylates, especially ethoxylates derived from primary alcohols, and blends thereof with more sophisticated surfactants, such as the polyoxypropylene/polyoxyethylene/polyoxypropylene reverse block polymers. In preferred embodiments the LFNI component is solid at about 95° F. (35° C.), more preferably solid at about 77° F. (25° C.). For ease of manufacture of granular ADD's, a preferred LFNI has a melting point between about 77° F. (25° C.) and about 140° F. (60° C.), more preferably between about 80° F. (26.6° C.) and 110° F. (43.3° C.).

In a preferred embodiment, the LFNI is an ethoxylated surfactant derived from the reaction of a monohydroxy alcohol or alkylphenol containing from about 8 to about 20 carbon atoms, excluding cyclic carbon atoms, with from about 6 to about 15 moles of ethylene oxide per mole of alcohol or alkyl phenol on an average basis.

A particularly preferred LFNI is derived from a straight chain fatty alcohol containing from about 16 to about 20 carbon atoms ($C_{16}$–$C_{20}$ alcohol), preferably a $C_{18}$ alcohol, condensed with an average of from about 6 to about 15 moles, preferably from about 7 to about 12 moles, and most preferably from about 7 to about 9 moles of ethylene oxide per mole of alcohol. Preferably the ethoxylated nonionic surfactant so derived has a narrow ethoxylate distribution relative to the average.

The LFNI can optionally contain propylene oxide in an amount up to about 15% by weight. Other preferred LFNI surfactants can be prepared by the processes described in U.S. Pat. No. 4,223,163, issued Sep. 16, 1980, Builloty, incorporated herein by reference.

Highly preferred ADDs herein wherein the LFNI is present make use of ethoxylated monohydroxy alcohol or alkyl phenol and additionally comprise a polyoxyethylene, polyoxypropylene block polymeric compound; the ethoxylated monohydroxy alcohol or alkyl phenol fraction of the LFNI comprising from about 20% to about 80%, preferably from about 30% to about 70%, of the total LFNI.

Suitable block polyoxyethylene-polyoxypropylene polymeric compounds that meet the requirements described hereinbefore include those based on ethylene glycol, propylene glycol, glycerol, trimethylolpropane and ethylenediamine as initiator reactive hydrogen compound. Polymeric compounds made from a sequential ethoxylation and propoxylation of initiator compounds with a single reactive hydrogen atom, such as $C_{12-18}$ aliphatic alcohols, do not generally provide satisfactory suds control in the instant ADDs. Certain of the block polymer surfactant compounds designated PLURONIC® and TETRONIC® by the BASF-Wyandotte Corp., Wyandotte, Mich., are suitable in ADD compositions of the invention.

A particularly preferred LFNI contains from about 40% to about 70% of a polyoxypropylene/polyoxyethylene/polyoxypropylene block polymer blend comprising about 75%, by weight of the blend, of a reverse block co-polymer of polyoxyethylene and polyoxypropylene containing 17 moles of ethylene oxide and 44 moles of propylene oxide; and about 25%, by weight of the blend, of a block copolymer of polyoxyethylene and polyoxypropylene initiated with trimethylolpropane and containing 99 moles of propylene oxide and 24 moles of ethylene oxide per mole of trimethylolpropane.

Suitable for use as LFNI in the ADD compositions are those LFNI having relatively low cloud points and high hydrophilic-lipophilic balance (HLB). Cloud points of 1% solutions in water are typically below about 32° C. and preferably lower, e.g., 0° C., for optimum control of sudsing throughout a full range of water temperatures.

LFNIs which may also be used include a $C_{18}$ alcohol polyethoxylate, having a degree of ethoxylation of about 8, commercially available as SLF18 from Olin Corp., and any biodegradable LFNI having the melting point properties discussed hereinabove.

Co-surfactant—Detergent compositions herein may optionally include co-surfactants such as anionic detersive surfactants, fatty alkyl glucosamides such as octyl-N-methylglucamine, amine oxides or the like, typically at levels of from about 0.1% to about 5% by weight of the composition although higher levels are possible, for example in rinse aid formulations. Certain anionic co-surfactants, particularly precipitatable fatty carboxylic acids and high-foaming types, are preferably avoided. If used, co-surfactants are typically of a type having good solubility in the presence of calcium, and more preferably, exhibit a limesoap dispersing action. Such anionic co-surfactants are further illustrated by sulfobetaines, alkyl(polyethoxy)sulfates (AES), alkyl (polyethoxy)carboxylates, and $C_6$–$C_{10}$ alkyl sulfates.

Chelating Agents—The compositions herein may also optionally contain one or more transition-metal selective sequestrants, "chelants" or "chelating agents", e.g., iron and/or copper and/or manganese chelating agents. If utilized, chelating agents or transition-metal-selective sequestrants will preferably comprise from about 0.01% to about 10%, more preferably from about 0.05% to about 1% by weight of the compositions herein. Chelating agents suitable for use herein can be selected from the group consisting of aminocarboxylates, phosphonates (especially the aminophosphonates), polyfunctionally-substituted aromatic chelating agents, and mixtures thereof. Without intending to be bound by theory, it is believed that the benefit of these materials is due in part to their exceptional ability to control iron, copper and manganese in washing solutions; other benefits include inorganic film prevention or scale inhibition. Commercial chelating agents for use herein include the DEQUEST® series, and chelants from Monsanto, DuPont, and Nalco, Inc.

Aminocarboxylates useful as optional chelating agents are further illustrated by ethylenediaminetetracetates, N-hydroxyethylethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and S substituted ammonium salts thereof. In general, chelant mixtures may be used for a combination of functions, such as multiple transition-metal control, long-term product stabilization, and/or control of precipitated transition metal oxides and/or hydroxides.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially (but not limited to) the [S,S] isomer as described in U.S. Pat. No. 4,704,233, Nov. 3, 1987, to Hartman and Perkins. The trisodium salt is preferred though other forms, such as magnesium salts, may also be useful.

Aminophosphonates are also suitable for use as chelating agents in the compositions of the invention when at least low levels of total phosphorus are permitted in detergent compositions, and include the ethylenediaminetetrakis (methylenephosphonates) and the diethylenetriaminepentakis (methylene phosphonates). Preferably, these aminophosphonates do not contain alkyl or alkenyl groups with more than about 6 carbon atoms.

Builders—Detergent builders other than silicates will typically be included in the compositions herein to assist in controlling mineral hardness. Inorganic as well as organic builders can be used. Builders are typically used in automatic dishwashing to assist in the removal of particulate soils.

The level of builder can vary widely depending upon the end use of the composition and its desired physical form. When present, the compositions will typically comprise at least about 1% builder. High performance compositions typically comprise from about 5% to about 80%, more typically from about 10% to about 40% by weight, of the detergent builder. Lower or higher levels of builder, however, are not excluded.

Inorganic or P-containing detergent builders include, but are not limited to, the alkali metal, ammonium and alkanolammonium salts of polyphosphates (exemplified by the tripolyphosphates, pyrophosphates, and glassy polymeric metaphosphates), phosphonates, phytic acid, silicates, carbonates (including bicarbonates and sesquicarbonates), sulfates, and aluminosilicates. However, non-phosphate builders are required in some locales. Compositions herein function surprisingly well even in the presence of "weak" builders (as compared with phosphates) such as citrate, or in the so-called "underbuilt" situation that may occur with zeolite or layered silicate builders. See U.S. Pat. No. 4,605,509 for examples of preferred aluminosilicates.

Examples of carbonate builders are the alkaline earth and alkali metal carbonates as disclosed in German Patent Application No. 2,321,001 published on Nov. 15, 1973. Various grades and types of sodium carbonate and sodium sesquicarbonate may be used, certain of which are particularly useful as carriers for other ingredients, especially detersive surfactants. Carbonates when used herein are preferably incorporated in conjunction with dispersant polymers disclosed hereinafter to minimize spotting/filming, especially on glass.

Citrate builders, e.g., citric acid and soluble salts thereof (particularly sodium salt), are polycarboxylate builders of particular importance for heavy duty laundry detergent and automatic dishwashing formulations due to their availability from renewable resources and their biodegradability. Citrates can also be used in combination with zeolite, the aforementioned BRITESIL types, and/or layered silicate or so-called "disilicate" builders. Oxydisuccinates are also useful in such compositions and combinations.

More generally, organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt or "overbased". When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediaminetetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Also suitable in the detergent compositions of the present invention are the 3,3-dicarboxy4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322.

Aluminosilicate builders may be used in the present compositions though are not preferred for automatic dishwashing detergents. These aluminosilicates can be crystalline or amorphous in structure and can be naturally-occurring aluminosilicates or synthetically-derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite & Zeolite P (B), Zeolite MAP and Zeolite X. Zeolite A is highly preferred. The degree of hydration of the zeolite and its particle size may vary. Preferably, the aluminosilicate has a particle size of about 0.1–10 microns in diameter. Individual particles can desirably be even smaller than 0.1 micron to further assist kinetics of exchange through maximization of surface area. High surface area also increases utility of aluminosilicates as adsorbents for surfactants, especially in granular compositions. Aggregates of silicate or aluminosilicate particles may be useful, a single aggregate having dimensions tailored to minimize segregation in granular compositions, while the aggregate particle remains dispersible to submicron individual particles during the wash. As with other builders such as carbonates, it may be desirable to use zeolites in any physical or morphological form adapted to promote surfactant carder function, and appropriate particle sizes may be freely selected by the formulator.

Fatty acids, such as the $C_{12}$–$C_{18}$ monocarboxylic acids, can also be incorporated into the compositions alone, or in combination with the aforesaid builders, especially citrate and/or the succinate builders. Fatty acids or their salts are however undesirable in Automatic Dishwashing (ADD) embodiments in situations wherein soap scums can form and be deposited on dishware. If used, branched fatty acids having a low Krafft temperature for the calcium salt are preferred.

Where phosphorus-based builders can be used, the various alkali metal phosphates such as the well-known sodium tripolyphosphates, sodium pyrophosphate and sodium orthophosphate can be used. Phosphonate builders such as ethane-1 -hydroxy-1,1-diphosphonate and other known phosphonates (see, for example, U.S. Pat. Nos. 3,159,581; 3,213,030; 3,422,021; 3,400,148 and 3,422,137) can also be used though such materials are more commonly used in a low-level mode as chelants or stabilizers.

Dispersant Polymer—Preferred automatic dishwashing (ADD) compositions herein may additionally contain a dispersant polymer. The equivalent term "polymeric dispersant" sometimes being used. When present, a dispersant polymer in the instant ADD compositions is typically at levels in the range from 0 to about 25%, preferably from about 0.5% to about 20%, more preferably from about 1% to about 8% by weight of the ADD composition. Dispersant polymers are useful for improved filming performance of the present ADD compositions, especially in higher pH embodiments, such as those in which wash pH exceeds about 9.5. Particularly preferred are polymers which inhibit the deposition of calcium carbonate or magnesium silicate on dishware.

Dispersant polymers suitable for use herein are further illustrated by the film-forming polymers described in U.S. Pat. No. 4,379,080 (Murphy), issued Apr. 5, 1983.

Suitable polymers are preferably at least partially neutralized salts of polycarboxylic acids. The alkali metal, especially sodium salts are most preferred. While the molecular weight of the polymer can vary over a wide range, it is typically in the range from about 1,000 to about 500,000, more preferably is from about 1,000 to about 250,000. More preferably, especially if the ADD is for use in North American automatic dishwashing appliances, suitable dispersant polymers have an average molecular weight of from about 1,000 to about 5,000.

Other suitable dispersant polymers include those disclosed in U.S. Pat. No. 3,308,067 issued Mar. 7, 1967, to Diehl. Unsaturated monomeric acids that can be polymerized to form suitable dispersant polymers include acrylic acid, maleic acid (or maleic anhydride), fumaric acid, itaconic acid, aconitic acid, mesaconic acid, citraconic acid and methylenemalonic acid. The presence of monomeric segments containing no carboxylate radicals such as methyl vinyl ether, styrene, ethylene, etc. is suitable but preferably such segments do not constitute more than about 50% by weight of the dispersant polymer.

Copolymers of acrylamide and acrylate having a molecular weight of from about 3,000 to about 100,000, preferably from about 4,000 to about 20,000, and an acrylamide content of less than about 50%, preferably less than about 20%, by weight of the dispersant polymer are suitable for use herein. Preferably, such dispersant polymer has a molecular weight of from about 4,000 to about 20,000 and an acrylamide content of from about 0% to about 15%, by weight of the polymer.

Another preferred group of dispersant polymers are low molecular weight modified polyacrylate copolymers. Such copolymers contain as monomer units: a) from about 90% to about 10%, preferably from about 80% to about 20% by weight acrylic acid or its salts and b) from about 10% to about 90%, preferably from about 20% to about 80% by weight of a substituted acrylic monomer or its salt and have the general formula: —[$(C(R^2)C(R^1)(C(O)OR^3)$)]— wherein the apparently unfilled valencies are in fact occupied by hydrogen and at least one of the substituents $R^1$, $R^2$, or $R^3$, preferably $R^1$ or $R^2$, is a 1 carbon to about a 4 carbon alkyl or hydroxyalkyl group; $R^1$ or $R^2$ may be hydrogen and $R^3$ may be hydrogen or alkali metal salt. Most preferred is a substituted acrylic monomer wherein $R^1$ is methyl, $R^2$ is hydrogen, and $R^3$ is sodium.

Suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and is the fully neutralized sodium salt form of the polymer comprising about 70% by weight acrylic acid and about 30% by weight methacrylic acid.

Other suitable modified polyacrylate copolymers include the low molecular weight copolymers of unsaturated aliphatic carboxylic acids disclosed in U.S. Pat. Nos. 4,530,766, and 5,084,535.

Agglomerated forms of the present ADD compositions may employ aqueous solutions of polymeric dispersants as liquid binders for making the agglomerate (particularly when the composition consists of a mixture of sodium titrate and sodium carbonate). Especially preferred are polyacrylates with an average molecular weight of from about 1,000 to about 10,000, and acrylate/maleate or acrylate/fumarate copolymers with an average molecular weight of from about 2,000 to about 80,000 and a ratio of acrylate to maleate or fumarate segments of from about 30:1 to about 1:2. Examples of such copolymers based on a mixture of unsaturated mono- and dicarboxylate monomers are disclosed in European Patent Application No. 66,915, published Dec. 15, 1982.

Other dispersant polymers useful herein include the polyethylene glycols and polypropylene glycols having a molecular weight of from about 950 to about 30,000 which can be obtained from the Dow Chemical Company of Midland, Mich. Such polymers for example, having a melting point within the range of from about 30° C. to about 100° C., can be obtained at molecular weights of 1,450, 3,400, 4,500, 6,000, 7,400, 9,500, and 20,000 and are formed by the polymerization of ethylene glycol or propylene glycol with the requisite number of moles of ethylene or propylene oxide to provide the desired molecular weight and melting point of the respective polyethylene glycol and polypropylene glycol. The polyethylene, polypropylene and mixed glycols are referred to using the formula:

$$HO(CH_2CH_2O)_m(CH_2CH(CH_3)O)_n(CH(CH_3)CH_2O)_oOH$$

wherein m, n, and o are integers satisfying the molecular weight and temperature requirements given above.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Other acceptable dispersant polymers are the carboxylated polysaccharides, particularly starches, celluloses and alginates, described in U.S. Pat. No. 3,723,322, Diehl, issued Mar. 27, 1973; the dextrin esters of polycarboxylic acids disclosed in U.S. Pat. No. 3,929,107, Thompson, issued Nov. 11, 1975; the hydroxyalkyl starch ethers, starch esters, oxidized starches, dextrins and starch hydrolysates described in U.S. Pat No. 3,803,285, Jensen, issued Apr. 9, 1974; the carboxylated starches described in U.S. Pat. No. 3,629,121, Eldib, issued Dec. 21, 1971; and the dextrin starches described in U.S. Pat. No. 4,141,841, McDonald, issued Feb. 27, 1979. Preferred cellulose-derived dispersant polymers are the carboxymethyl celluloses.

Yet another group of acceptable dispersants are the organic dispersant polymers, such as polyaspartate although any potentially bleach-reactive polymer or other ingredient is not preferred for use herein.

Detersive Enzymes—"Detersive enzyme", as used herein, means any enzyme having a cleaning, stain removing or otherwise beneficial effect in an ADD composition. Preferred detersive enzymes are hydrolases such as proteases, amylases and lipases. Highly preferred for automatic dishwashing are amylases and/or proteases, including both current commercially available types and improved types which, though more bleach compatible, have a remaining degree of bleach deactivation susceptibility.

In general, as noted, preferred ADD compositions herein comprise one or more detersive enzymes. If only one enzyme is used, it is preferably an amyolytic enzyme when the composition is for automatic dishwashing use. Highly preferred for automatic dishwashing is a mixture of proteolytic enzymes and amyloytic enzymes.

More generally, the enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders, etc. In this respect bacterial or fungal enzymes are preferred, such as bacterial amylases and proteases, and fungal cellulases.

Enzymes are normally incorporated in the instant detergent compositions at levels sufficient to provide a "cleaning-effective amount". The term "cleaning-effective amount" refers to any amount capable of producing a cleaning, stain removal or soil removal effect on substrates such as fabrics, dishware and the like. Since enzymes are catalytic materials, such amounts may be very small. In practical terms for current commercial preparations, typical amounts are up to about 5 mg by weight, more typically about 0.01 mg to about 3 mg, of active enzyme per gram of the composition. Stated otherwise, the compositions herein will typically comprise from about 0.0001% to about 10%, preferably 0.01%–1% by weight of a commercial enzyme preparation. Protease enzymes are usually present in such commercial preparations at levels sufficient to provide from 0.005 to 0.1 Anson units (AU) of activity per gram of composition. For automatic dishwashing purposes, it may be desirable to increase the active enzyme content of the commercial preparations, in order to minimize the total amount of non-catalytically active materials delivered and thereby improve spotting/filming results.

Suitable examples of proteases are the subtilisins which are obtained from particular strains of *B. subtilis* and *B. licheniformis*. Another suitable protease is obtained from a strain of Bacillus, having maximum activity throughout the pH range of 8–12, developed and sold by Novo Industries A/S as ESPERASE®. The preparation of this enzyme and analogous enzymes is described in British Patent Specification No. 1,243,784 of Novo. Proteolytic enzymes suitable for removing protein-based stains that are commercially available include those sold under the tradenames ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

An especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, 104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in the patent applications of A. Baeck, et al, entitled "Protease-Containing Cleaning Compositions" having U.S. Ser. No. 08/322,676, and C. Ghosh, et al, "Bleaching Compositions Comprising Protease Enzymes" having U.S. Ser. No. 08/322,677, both filed Oct. 13, 1994.

Amylases suitable herein include, for example, α-amylases described in British Patent Specification No. 1,296,839

(Novo), RAPIDASE®, International Bio-Synthetics, Inc. and TERMAMYL®, Novo Industries.

Engineering of enzymes (e.g., stability-enhanced amylase) for improved stability, e.g., oxidative stability is known. See, for example J. Biological Chem., Vol. 260, No. 11, June 1985, pp 6518–6521. "Reference amylase" refers to a conventional amylase inside the scope amylases useful in this invention. Further, stability-enhanced amylases, also useful herein, are typically superior to these "reference amylases".

The present invention, in certain preferred embodiments, can makes use of amylases having improved stability in detergents, especially improved oxidative stability. A convenient absolute stability reference-point against which amylases used in these preferred embodiments of the instant invention represent a measurable improvement is the stability of TERMAMYL® in commercial use in 1993 and available from Novo Nordisk A/S. This TERMAMYL® amylase is a "reference amylase", and is itself well-suited for use in the ADD (Automatic Dishwashing Detergent) compositions of the invention, as well as in inventive fabric laundering compositions herein. Even more preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, all measured versus the above-identified reference-amylase. Preferred amylases herein can demonstrate further improvement versus more challenging reference amylases, the latter reference amylases being illustrated by any of the precursor amylases of which preferred amylases within the invention are variants. Such precursor amylases may themselves be natural or be the product of genetic engineering. Stability can be measured using any of the an-disclosed technical tests. See references disclosed in WO 94/02597, itself and documents therein referred to being incorporated by reference.

In general, stability-enhanced amylases respecting the preferred embodiments of the invention can be obtained from Novo Nordisk A/S, or from Genencor International.

Preferred amylases herein have the commonality of being derived using site-directed mutagenesis from one or more of the Baccillus amylases, especialy the Bacillus alpha-amylases, regardless of whether one, two or multiple amylase strains are the immediate precursors.

As noted, "oxidative stability-enhanced" amylases are preferred for use herein despite the fact that the invention makes them "optional but preferred" materials rather than essential. Such amylases are non-limitingly illustrated by the following:

(a) An amylase according to the hereinbefore incorporated WO/94/02597, Novo Nordisk A/S, published Feb. 3, 1994, as further illustrated by a mutant in which substitution is made, using alanine or threonine (preferably threonine), of the methionine residue located in position 197 of the *B. licheniformis* alpha-amylase, known as TERMAMYL®, or the homologous position variation of a similar parent amylase, such as *B. amyloliquefaciens, B. subtilis,* or *B. stearothermophilus;*

(b) Stability-enhanced amylases as described by Genencor International in a paper entitled "Oxidatively Resistant alpha-Amylases" presented at the 207th American Chemical Society National Meeting, Mar. 13–17 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8,15,197,256,304,366 and 438 leading to specific mutants, particularly important being M197L and M197T with the M197T variant being the most stable expressed variant. Stability was measured in CASCADE® and SUNLIGHT®;

(c) Particularly preferred herein are amylase variants having additional modification in the immediate parent available from Novo Nordisk A/S. These amylases do not yet have a tradename but are those referred to by the supplier as QL37+M197T.

Any other oxidative stability-enhanced amylase can be used, for example as derived by site-directed mutagenesis from known chimeric, hybrid or simple mutant parent forms of available amylases.

Cellulases usable in, but not preferred, for the present invention include both bacterial or fungal cellulases. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from *Humicola insolens* and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS-2.247.832. CAREZYME® (Novo) is especially useful.

Suitable lipase enzymes for detergent use include those produced by microorganisms of the Pseudomonas group, such as *Pseudomonas stutzeri* ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum var. lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli.* The LIPOLASE® enzyme derived from *Humicola lanuginosa* and commercially available from Novo (see also EPO 341,947) is a preferred lipase for use herein. Another preferred lipase enzyme is the D96L variant of the native *Humicola lanuginosa* lipase, as described in WO 92/05249 and Research Disclosure No. 35944, Mar. 10, 1994, both published by Novo. In general, lipolytic enzymes are less preferred than amylases and/or proteases for automatic dishwashing embodiments of the present invention.

Peroxidase enzymes can be used in combination with oxygen sources, e.g., percarbonate, perborate, persulfate, hydrogen peroxide, etc. They are typically used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S. The present invention encompasses peroxidase-free automatic dishwashing composition embodiments.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

Adjuncts Further Complementing $H_2O_2$ Source and Selected Bleach Activator (a) Bleach catalysts—If desired, detergent compositions herein may additionally incorporate a catalyst or accelerator to further improve bleaching or starchy soil removal. Any suitable bleach catalyst can be used. For detergent compositions used at a total level of from about 1,000 to about 5,000 ppm in water, the composition will typically deliver a concentration of from about 0.1 ppm to about 700 ppm, more preferably from about 1 ppm to about 50 ppm, or less, of the catalyst species in the wash liquor. Cobalt catalysts described hereinbelow are more preferably at a level of from about 2 ppm to about 10 ppm of the wash liquor.

Typical bleach catalysts comprise a transition-metal complex, for example one wherein the metal co-ordinating ligands are quite resistant to labilization and which does not deposit metal oxides or hydroxides to any appreciable extent under the typically alkaline conditions of machine dishwashing. Such catalyst compounds often have features of naturally occurring compounds such as enzymes but are principally provided synthetically. Highly preferred accelerators include, for example, the cobalt 3+ catalysts, especially $\{Co(NH_3)_5Cl\}^{2+}$ or equivalents thereof with various alternate donor ligands. Such complexes include those formerly disclosed for use in laundry compositions in U.S. Pat. No. 4,810,410 to Diakun et al, issued Mar. 7, 1989, incorporated herein by reference and are unexpectedly superior in an automatic dishwashing application. The active species thereof is believed to be $\{Co(NH_3)_5(OOH)\}^{2+}$ and is disclosed in J. Chem. Soc. Faraday Trans., 1994, Vol. 90, 1105–1114, herein incorporated by reference. Alternate catalysts or accelerators are the noncobalt transition metal complexes disclosed in this reference, especially those based on Mo(VI), Ti(IV), W(VI), V(V) and Cr(VI) although alternate oxidation states and metals may also be used. Such catalysts include manganese-based catalysts disclosed in U.S. Pat. Nos. 5,246,621, 5,244,594; 5,194,416; 5,114,606; and EP Nos. 549,271 A1, 549,272 A1, 544,440 A2, and 544,490 A1; preferred examples of these catalysts include $Mn^{IV}_2(\mu\text{-}O)_3(TACN)_2\text{-}(PF_6)_2$, $Mn^{III}_2(\mu\text{-}O)_1(\mu\text{-}OAc)_2(TACN)_2(ClO_4)_2$, $Mn^{IV}_4$ $(\mu\text{-}O)_6(TACN)_4(ClO_4)_4$, $Mn^{III}Mn^{IV}_4\text{-}(\mu\text{-}O)_1(\mu\text{-}OAc)_2$ -$(TACN)_2\text{-}(ClO_4)_3$, $Mn^{IV}\text{-}(TACN)\text{-}(OCH_3)_3(PF_6)$, and mixtures thereof wherein TACN is trimethyl-1,4,7-triazacyclononane or an equivalent macrocycle; though alternate metal-co-ordinating ligands as well as mononuclear complexes are also possible and monometallic as well as di- and polymetallic complexes and complexes of alternate metals such as iron or ruthenium are all within the present scope. Other metal-based bleach catalysts include those disclosed in U.S. Pat. Nos. 4,430,243 and 5,114,611. The use of manganese with various complex ligands to enhance bleaching is also reported in the following U.S. Pat. Nos.: 4,728,455; 5,284,944; 5,246,612; 5,256,779; 5,280,117; 5,274,147; 5,153,161; and 5,227,084.

Transition matals may be precomplexed or complexed in-situ with suitable donor ligands selected in function of the choice of metal, its oxidation state and the denticity of the ligands. Other complexes which may be included herein are those of U.S. application Ser. No. 08/210,186, filed Mar. 17, 1994. Other suitable transition metals in said transition-metal-containing bleach catalysts include iron, cobalt, ruthenium, rhodium, iridium, and copper.

(b) Conventional Bleach Activators—"Conventional Bleach Activators" herein are any bleach activators not encompassed within the definition of the essential bleach activator component and are optional materials for the inventive compositions. If used, they will typically be supplements rather than replacements for the inventive combinations. Suitable levels are from about 0.1% to about 8% of the detergent composition. Such activators are any known activators not specifically included in the essential bleach activator component and are typified by TAED (tetraacetylethylenediamine). Numerous conventional activators are known. See for example activators referenced hereinabove in the background as well as U.S. Pat. No. 4,915,854, issued Apr. 10, 1990 to Mao et al, and U.S. Pat. No. 4,412,934. Nonanoyloxybenzenesulfonate (NOBS) or acyl lactam activators may be used, and mixtures thereof with TAED can also be used. See also U.S. Pat. No. 4,634,551 for other typical conventional bleach activators. Also known are amido-derived bleach activators of the formulae: $R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. Further illustration of bleach activators of the above formulae include (6-octanamidocaproyl)oxybenzenesulfonate, (6-nonanamidocaproyl)oxybenzenesulfonate, (6-decanamidocaproyl)oxybenzenesulfonate, and mixtures thereof as described in U.S. Pat. No. 4,634,551. Another class of bleach activators comprises the benzoxazin-type activators disclosed by Hodge et al in U.S. Pat. No. 4,966,723, issued Oct. 30, 1990. Still another class of bleach activators includes acyl lactam activators such as octanoyl caprolactam, 3,5,5-trimethylhexanoyl caprolactam, nonanoyl caprolactam, decanoyl caprolactam, undecenoyl caprolactam, octanoyl valerolactam, decanoyl valerolactam, undecenoyl valerolactam, nonanoyl valerolactam, 3,5,5-trimethylhexanoyl valerolactam, t-butylbenzoylcaprolactam, t-butylbenzoylvalerolactam and mixtures thereof. The present compositions can optionally comprise aryl benzoates, such as phenyl benzoate. When such an activator is added to the instant compositions, it is preferably of a low-foaming and non-depositing type.

(c) Organic Peroxides, especially Diacyl Peroxides— These are extensively illustrated in Kirk Othmer, Encyclopedia of Chemical Technology, Vol. 17, John Wiley and Sons, 1982 at pages 27–90 and especially at pages 63–72, all incorporated herein by reference. If a diacyl peroxide is used, it will preferably be one which exerts minimal adverse impact on spotting/filming.

Material Care Agents—The present compositions may contain as corrosion inhibitors and/or anti-tarnish aids one or more material care agents other than the hereinbefore referenced silicates. Material Care Agents are preferred especially in countries where electroplated nickel silver and sterling silver are common in domestic flatware, or when aluminium protection is a concern and the composition is low in silicate. Material care agents include bismuth salts, transition metal salts such as those of manganese, certain types of paraffin, triazoles, pyrazoles, thiols, mercaptans, aluminium fatty acid salts, and mixtures thereof and are preferably incorporated at low levels, e.g., from about 0.01% to about 5% of the ADD composition. A preferred paraffin oil is a predominantly branched aliphatic hydrocarbon comprising from about 20 to about 50, more preferably from about 25 to about 45, carbon atoms with a ratio of cyclic to noncyclic hydrocarbons of about 32 to 68 sold by Wintershall, Salzbergen, Germany as WINOG 70®. $Bi(NO_3)_3$ may be added. Other corrosion inhibitors are illustrated by benzotriazole, thiols including thionaphtol and thioanthranol, and finely divided aluminium fatty acid salts. All such materials will generally be used judiciously so as to avoid producing spots or films on glassware or compromising the bleaching action of the compositions. For this reason, it may be preferred to formulate without mercaptan antitarnishes which are quite strongly bleach-reactive or common fatty carboxylic acids which precipitate with calcium.

Silicone and Phosphate Ester Suds Suppressors—The automatic dishwashing compositions of the invention can optionally contain an alkyl phosphate ester suds suppressor, a silicone suds suppressor, or combinations thereof. Levels in general are from 0% to about 10%, preferably, from about 0.001% to about 5%. Typical levels tend to be low, e.g., from about 0.01% to about 3% when a silicone suds suppressor is used. Preferred non-phosphate compositions omit the phosphate ester component entirely. Silicone suds suppressor technology and other defoaming agents useful herein are more extensively documented in "Defoaming, Theory and Industrial Applications", Ed., P. R. Garrett, Marcel Dekker, N.Y., 1973, ISBN 0-8247-8770-6, incorporated herein by reference. See especially the chapters entitled "Foam control in Detergent Products" (Ferch et al) and "Surfactant Antifoams" (Blease et al). See also U.S. Pat. Nos. 3,933,672 and 4,136,045. Highly preferred silicone suds suppressors are the compounded types known for use in laundry detergents such as heavy-duty granules, although types hitherto used only in heavy-duty liquid detergents may also be incorporated in the instant compositions. For example, polydimethylsiloxanes having trimethylsilyl or alternate endblocking units may be used as the silicone. These may be compounded with silica and/or with surface-active nonsilicon components, as illustrated by a suds suppressor comprising 12% silicone/silica, 18% stearyl alcohol and 70% starch in granular form. A suitable commercial source of the silicone active compounds is Dow Corning Corp.

Phosphate esters have also been asserted to provide some protection of silver and silver-plated utensil surfaces; however, the instant compositions can have excellent silvercare without a phosphate ester component. If it is desired nonetheless to use a phosphate ester, suitable compounds are disclosed in U.S. Pat. No. 3,314,891, issued Apr. 18, 1967, to Schmolka et al, incorporated herein by reference. Preferred alkyl phosphate esters contain from 16–20 carbon atoms. Highly preferred alkyl phosphate esters are monostearyl acid phosphate or monooleyl acid phosphate, or salts thereof, particularly alkali metal salts, or mixtures thereof.

It has been found preferable to avoid the use of simple calcium-precipitating soaps as antifoams in the present compositions as they tend to deposit on the dishware. Indeed, phosphate esters are not entirely free of such problems and the formulator will generally choose to minimize the content of potentially depositing antifoams in the instant compositions.

Other Ingredients—Detersive ingredients or adjuncts optionally included in the instant compositions can include one or more materials for assisting or enhancing cleaning performance, treatment of the substrate to be cleaned, or designed to improve the aesthetics or ease of manufacture of the compositions. The fully-formulated product is desirably tested to ensure acceptable levels of spotting/filming and good foam control. Other adjuncts which can also be included in compositions of the invention at their conventional art-established levels, generally from 0% to about 20% of the composition, preferably at from about 0.1% to about 10%, include color speckles, dyes, fillers, germicides, alkalinity sources, hydrotropes, stabilizers, perfumes, solubilizing agents, carders, processing aids, and, for liquid formulations, solvents.

pH and Buffering Variation—In preferred embodiments, the present compositions comprise a combination of ingredients selected so that when the composition is dissolved in water at typical use concentrations of from about 1,000 ppm to about 5,000 ppm, the pH remains in the range of above about 8, preferably from about 9.5 to about 11. Compact formulations are those for which usage concentration in U.S. domestic dishwashers is more typically from about 1,500 to about 3,500 ppm. Many detergent compositions herein will be buffered, i.e., they are relatively resistant to pH drop in the presence of acidic soils. However, other compositions herein, nonlimitingly illustated by rinse aids, may be substantially unbuffered. Techniques for controlling or varying pH at recommended usage levels more generally include the use of not only buffers, but also additional alkalis, acids, pH-jump systems, dual compartment containers, etc., known to those skilled in the art. Detergent compositions herein in granular form typically limit water content, for example to less than about 7% free water, for best storage stability. Storage stability can be further enhanced by limiting the content in the compositions of adventitious redox-active substances such as rust and other traces of transition metals in undesirable form. Certain compositions may moreover be limited in their total halide ion content, or may have any particular halide, e.g., bromide, substantially absent. Bleach stabilizers such as stannates can be added for improved stability and formulations may be substantially nonaqueous if desired.

Coating—Various detersive ingredients employed in the present compositions optionally can be further stabilized by absorbing said ingredients onto a porous hydrophobic substrate, then coating or encapsulating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT®D 10, Degussa) is admixed with a proteolytic enzyme solution containing 3%–5% of $C_{13.15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Spotting/Filming and Foam Control—Preferred compositions have spotting and filming grades of 3 or less, preferably less than 2, and most preferably less than 1, as measured by the standard test of The American Society for Testing and Materials ("ASTM") D3556–85 (Reapproved 1989) "Standard Test Method for Deposition on Glassware During Mechanical Dishwashing".

Preferred compositions moreover produce less than 2 inches, more preferably less than 1 inch, of suds in the bottom of a domestic spray-arm type automatic dishwasher during normal use conditions (as determined using known methods such as, for example, that described in U.S. Pat. No. 5,294,365, to Welch et al., issued Mar. 15, 1994). Foam control can also desirably be measured by counting spray-arm rotation: preferred compositions have minimal impact on arm rotation.

EXAMPLE I

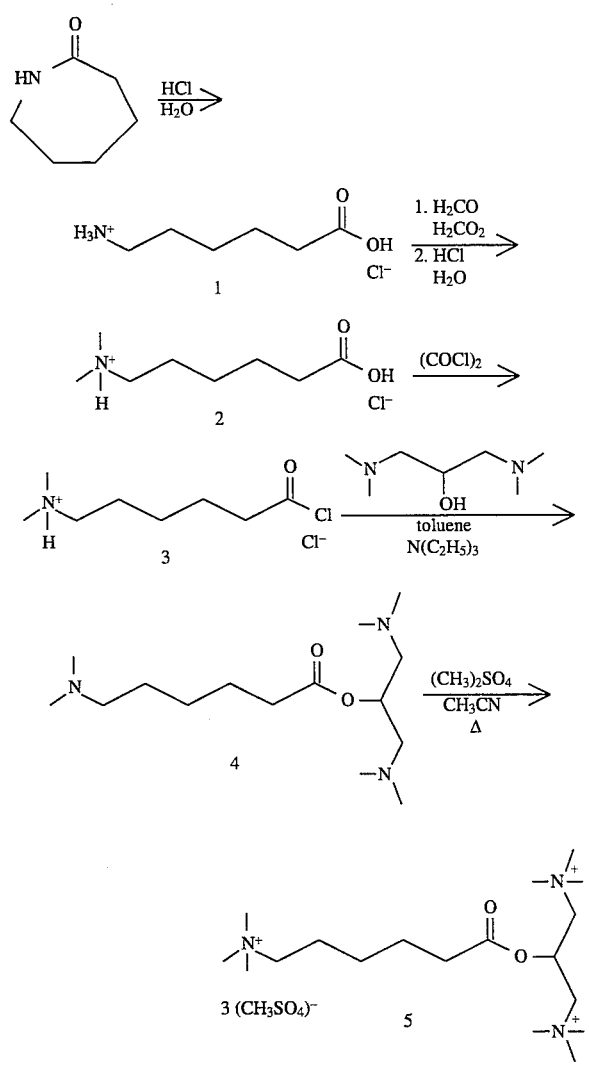

6-Aminohexanoic Acid Hydrochloride (1)

ε-Caprolactam (750.00 g, 6.63 mol), water (1500 mL), and concentrated HCl (675 mL, 36–38%) are combined in a 5000 mL three-necked round bottomed flask fitted with a mechanical stirrer and condenser. The mixture is heated for 4 h at reflux, cooled to room temperature, and concentrated by rotary evaporation at 50° C. (water aspirator vacuum) to give 1 as a white solid. The absence of ε-caprolactam by TLC ($R_f$=0.21, THF) indicates the reaction is complete.

6-(N,N-Dimethylamino)hexanoic Acidhydrochloride (2)

6-Aminohexanoic acidhydrochloride (1204 g, 6.63 mol, 92%—balance being water), formaldehyde (577.37 g, 19.23 mol, 37 wt %), and formic acid (1739.50 g, 37.79 mol, 88%) are divided into two 5000 mL three-necked round-bottomed flasks each fitted with a condenser and magnetic stirrer. Each mixture is heated at reflux for 21 h, cooled to room temperature, and treated with concentrated HCl (226 mL, 36–38% in each flask). The combined reaction mixtures are concentrated to near dryness by rotary evaporation for 3 h at 70° C. and then further concentrated in a Kugelrohr oven at 60° C. for 2 h to give 2, 1202.68 g (93% based on ε-caprolactam starting material) of a white crystalline solid.

6-(N,N-Dimethylamino)hexanoyl Chloridehydrochloride (3)

Oxalyl chloride (3367.33 g, 26.53 mol) is placed in a 5000 mL three-necked round-bottomed flask equipped with a reflux condenser, internal thermometer, mechanical stirrer, and argon inlet. 6-(N,N-Dimethylamino)hexanoic acidhydrochloride (1146.00 g, 5.86 mol) is added over 3 h while maintaining the reaction temperature between 25–35° C. As reaction takes place, HCl, $CO_2$, and CO are swept away from the mixture with argon. After addition is complete, the mixture is cooled to room temperature over 45 min. Excess oxalyl chloride is removed first by rotary evaporation at 50° C. (water aspirator vacuum) and then by Kugelrohr distillation at 60° C. (0.3 mm Hg) for 3 h. A quantitative yield of 3 is isolated as a dark red oil that solidifies on standing.

2-[6'-(N,N-Dimethylamino)hexanoyloxy]-N,',N',N",N"-tetramethyl-1,3-propanediamine (4)

Into a 250 mL three-necked round-bottomed flask equipped with a condenser, mechanical stirrer, argon inlet, and addition funnel are placed 1,3-bis(dimethylamino)-2-propanol (10.00 g, 68.4 mmol), toluene (100 mL), and triethylamine (16.75 g, 165.5 mmol). The mixture is brought to reflux and treated with a solution of 6-(N,N-dimethylamino)hexanoyl chloridehydrochloride (16.11 g, 75.2 mmol) dissolved in dichloromethane (20 mL) over 30 min. After refluxing 3 h, the cooled mixture is filtered and the filter cake washed with toluene until the washings are colorless. The combined filtrate and washings are extracted with saturated sodium bicarbonate solution (2×100 mL), water (100 mL), dried over $MgSO_4$, and filtered. The solution is concentrated by rotary evaporation to give a brown oil. The resulting oil is distilled by Kugelrohr distilation (80°–90° C., 0.05 mmHg) to give 8.14 g (41.4%) of 4.

N,N,N,N',N',N'-Hexamethyl-2-[6'O(N",N",N"-trimethylammonio)hexanoyloxy]-1,3-propanediammonium Tri(methylsulfate) (5)

2-[6'-(N,N-Dimethylamino)hexanoyloxy]-N',N',N",N"-tetramethyl-1,3-propanediamine (8.13 g, 28.3 mmol) and acetonitrile (50 mL) are placed in a 100 mL round bottomed flask. Dimethyl sulfate (10.70 g, 84.8 mmol) is added and the mixture heated to reflux for 3 h under argon. The cooled mixture is poured into ether (500 mL) and stirred. The product crystallizes in the solution. The product is collected by vacuum filtration affording 18.08 g (96.0%) of 5 as a white solid.

EXAMPLE II

N,N,N,N',N',N'-Hexamethyl-2-[6'-(N'',N'',N''-trimethylammonio)hexanoyloxy]-1,3-propanediammonium Trichloride (6)

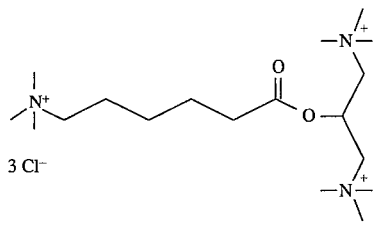

2-[6'-(N,N-Dimethylamino)hexanoyloxy]-N',N',N'',N''-tetramethyl-1,3-propanediamine (26.00 g, 90.5 mmol) and acetonitrile (30 mL) are placed in a glass autoclave liner. The liner is placed in an autoclave and its contents are treated with methyl chloride gas (65 psig, 65°–85° C.) for 18 h. The cooled mixture is poured into ether (500 mL) and stirred. The product crystallizes in the solution and is collected by vacuum filtration affording 25.35 g (63.9%) of 6 as a white solid.

EXAMPLE III

N,N,N,N',N',N'-Hexamethyl-2-[2'-(N'',N'',N''-trimethylammonio)ethanoyloxy]-1,3-propanediammonium Trichloride (7)

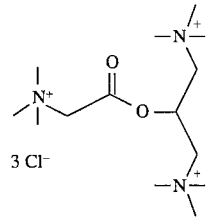

The synthesis of Example 1 is repeated with the substitution of 2-(N,N-dimethylamino)ethanoyl chloridehydrochloride for 6-(N,N-dimethylamino)hexanoyl chloride.hydrochloride.

EXAMPLE IV

Bleaching compositions having liquid form are as follows:

| Example IV Ingredients | A wt % | B wt % | C wt % | D wt % |
|---|---|---|---|---|
| Water | 76 | 81 | 84 | 70 |
| NEODOL 91-10[1] | 10 | 10 | 10 | 10 |
| NEODOL 23-2[1] | — | — | — | 5 |
| DEQUEST 2010[2] | 0.5 | 0.1 | 0.1 | 1.0 |
| Bleach Activator[3] | 6 | 6 | 4 | 7 |
| Citric Acid | 0.5 | 0.5 | 0.5 | 0.5 |
| NaOH | to pH 4 | to pH 4 | to pH 4 | to pH 4 |
| Hydrogen Peroxide | 7 | 3 | 2 | 7 |

[1]Alkyl ethoxylate available from The Shell Oil Company.

| Example IV Ingredients | A wt % | B wt % | C wt % | D wt % |
|---|---|---|---|---|

[2]Hydroxy-ethylidene diphosphonic acid commercially available from Monsanto Co.
[3]Multiquaternary bleach activator according to any of Examples I–III, preferably encapsulated or coated.

EXAMPLE V

A simple bleach additive for detergents is formulated as follows:

|  | wt % |
|---|---|
| Sodium Sulfate | 80 |
| Bleach Activator of Example I | 20 |

The additive is used in conjunction with a sodium perborate-containing commercial automatic dishwashing detergent, with excellent results.

EXAMPLE VI

A simple Automatic Dishwashing Detergent with Multiquaternary Bleach Activator is prepared by mixing:

| INGREDIENTS | wt % |
|---|---|
| Multiquaternary Bleach Activator: Compound of any of Examples I–III | 4 |
| Hydrogen Peroxide Source: Sodium Perborate Monohydrate | 15 |
| Silicate: BRITESIL H2O ®, PQ Corp. (as SiO$_2$) | 15 |
| Polymeric Dispersant (See Note 1) | 5 |
| Low Foaming Nonionic Surfactant (See Note 2) | 2 |
| Builder: Trisodium Citrate Dihydrate (anhydrous basis) | 20 |
| Chelant Mixture: EDDS/HEDP 1:1 | 2 |
| Builder: Sodium Carbonate (anhydrous basis) | 10 |
| Sodium Sulfate, water, minors | Balance to 100% |

Note 1: One or more of: Sokolan PA30 ®, BASF or Accusol 480N ®, Rohm & Haas.
Note 2: SLF18 ®, Olin Corp. or LF404 ®, BASF.

EXAMPLE VII

A commercial rinse-aid block sold as "Jet-Dry" is modified as follows: The rinse aid block and about 5%–20% of a bleach activator according to any of Examples I–III are comelted, mixed and resolidified into block form. The resulting cleaning composition is used in an automatic dishwashing appliance with excellent spotting/filming and stain removal results. In this mode, the bleach activators complement and boost the bleaching action delivered by conventional automatic dishwashing products comprising a source of hydrogen peroxide.

EXAMPLE VIII

Cleaning compositions having liquid form especially useful for cleaning bathtubs and shower tiles are as follows:

| Ingredient | % (wt.) A | B |
|---|---|---|
| Bleach Activator* | 7.0 | 5.0 |

-continued

| Ingredient | % (wt.) A | B |
|---|---|---|
| Hydrogen Peroxide | 10.0 | 10.0 |
| $C_{12}AS$, acid form, partially neutralized | 5.0 | 5.0 |
| $C_{12-14}AE_3S$, acid form, partially neutralized | 1.5 | 1.5 |
| $C_{12}$ Dimethylamine N-Oxide | 1.0 | 1.0 |
| DEQUEST 2060 | 0.5 | 0.5 |
| Citric acid | 5.5 | 6.0 |
| Abrasive (15-25 micron) | 15.0 | 0 |
| HCl | to pH 4 | |
| Filler and water | Balance to 100% | |

*Bleach Activator according to any of Examples I–III, coated with impermeable film.

EXAMPLE IX

Liquid bleaching compositions for cleaning typical household surfaces are as follows. The hydrogen peroxide is separated as an aqueous solution from the other components by any suitable means, such as a dual-chamber container.

| Component | A (wt %) | B (wt %) |
|---|---|---|
| $C_{8-10}E_6$ nonionic surfactant | 20 | 15 |
| $C_{12-13}E_3$ nonionic surfactant | 4 | 4 |
| $C_8$ alkyl sulfate anionic surfactant | 0 | 7 |
| $Na_2CO_3/NaHCO_3$ | 1 | 2 |
| $C_{12-18}$ Fatty Acid | 0.6 | 0.4 |
| Hydrogen peroxide | 7 | 7 |
| Bleach Activator* | 7 | 7 |
| DEQUEST 2060** | 0.05 | 0.05 |
| $H_2O$ | Balance to 100 | Balance to 100 |

*Bleach Activator according to any of Examples I–IIII, preferably encapsulated or coated.
**Commercially available from Monsanto Co.

EXAMPLE X

| INGREDIENTS | A wt % | B wt % |
|---|---|---|
| Multiquaternary Bleach Activator: Compound of any of Examples I–III | 4 | 1 |
| Hydrogen Peroxide Source: Sodium Perborate Monohydrate | 10 | 30 |
| Silicate: BRITESIL H2O ®, PQ Corp. (as $SiO_2$) | 12 | 8 |
| Silicate: Sodium Metasilicate, granular | 0 | 1 |
| Polymeric Dispersant (See Note 1) | 8 | 4 |
| Low Foaming Nonionic Surfactant (See Note 2) | 1 | 4 |
| Chelant: Hydroxyethyldiphosphonate (HEDP), Sodium Salt | 0 | 0.5 |
| Builder: Trisodium Citrate Dihydrate (anhydrous basis) | 10 | 20 |
| Builder: Sodium Carbonate (anhydrous basis) | 20 | 10 |
| Detersive Enzymes (Mixture of Savinase ® and Termamyl ®) | 2 | 4 |
| Sodium Sulfate, water, minors | Balance to 100% | Balance to 100% |

Note 1: One or more of: Sokolan PA30 ®, BASF or Accusol 480N ®, Rohm & Haas.
Note 2: SLF18 ®, Olin Corp. or LF404 ®, BASF.

EXAMPLE XI

| Example XI INGREDIENTS | A wt % | B wt % | C wt % |
|---|---|---|---|
| Multiquaternary Bleach Activator Compound of any of Examples I–III | 1 | 2 | 5 |
| Hydrogen Peroxide Source: Sodium Perborate Monohydrate | 0 | 0 | 20 |
| Hydrogen Peroxide Source: Sodium Percarbonate | 10 | 20 | 0 |
| Conventional Bleach Activator: TAED | 1 | 0 | 0 |
| Bleach Catalyst $\{Co(NH_3)_5Cl\}Cl_2$ | 0 | 0.1 | 0 |
| Silicate: BRITESIL H2O ®, PQ Corp. (as $SiO_2$) | 8 | 9 | 10 |
| Silicate: Sodium Metasilicate, granular | 0 | 0 | 1 |
| Low Foaming Nonionic Surfactant (See Note 2) | 1 | 2 | 3 |
| Polymeric Dispersant (See Note 1) | 3 | 5 | 6 |
| Benzoyl Peroxide | — | — | — |
| Chelant: Hydroxyethyldiphosphonate (HEDP), Sodium Salt | 0.5 | 0.5 | 0 |
| Chelant: Ethylenediamine Disuccinate, Trisodium Salt | 0.1 | 0 | 0.1 |
| Chelant: Diethylenetriaminepentaacetic acid, Pentasodium | 0 | 0.1 | 0 |
| Builder: Trisodium Citrate Dihydrate (anhydrous basis) | 10 | 15 | 10 |
| Builder: Sodium Carbonate (anhydrous basis) | 10 | 15 | 20 |
| Detersive Enzyme: Savinase ® 12T | 3 | 1 | 2 |
| Detersive Enzyme: Termamyl ® 60T | 0 | 1 | 1.5 |
| Paraffin/Benzotriazole | 0 | 0 | 0 |
| Sodium Sulfate, water, minors - Balance to: | 100 | 100 | 100 |

| Example XI, cont. INGREDIENTS | D wt % | E wt % | F wt % |
|---|---|---|---|
| Multiquaternary Bleach Activator Compound of any of Examples I–III | 3 | 3 | 5 |
| Hydrogen Peroxide Source: Sodium Perborate Monohydrate | 15 | 10 | 20 |
| Hydrogen Peroxide Source: Sodium Percarbonate | 0 | 0 | 0 |
| Conventional Bleach Activator: TAED | 0 | 0 | 0 |
| Bleach Catalyst $\{Co(NH_3)_5Cl\}Cl_2$ | 0 | 0 | 0 |
| Silicate: BRITESIL H2O ®, PQ Corp. (as $SiO_2$) | 12 | 8 | 10 |
| Silicate: Sodium Metasilicate, granular | 0 | 1 | 1 |
| Low Foaming Nonionic Surfactant (See Note 2) | 4 | 1 | 3 |
| Benzoyl Peroxide | — | — | 3 |
| Polymeric Dispersant (See Note 1) | 4 | 8 | 6 |
| Chelant: Hydroxyethyldiphosphonate (HEDP), Sodium Salt | 0.5 | 0.5 | 0.5 |
| Chelant: Ethylenediamine Disuccinate, Trisodium Salt | 0 | 0.1 | 0 |
| Chelant: Diethylenetriaminepentaacetic acid, Pentasodium | 0.1 | 0 | 0.1 |
| Builder: Trisodium Citrate Dihydrate (anhydrous basis) | 10 | 20 | 10 |
| Builder: Sodium Carbonate (anhydrous basis) | 10 | 30 | 20 |
| Detersive Enzyme: Savinase ® 12T | 0 | 2 | 2 |
| Detersive Enzyme: Termamyl ® 60T | 3 | 2 | 2 |
| Paraffin/Benzotriazole | 0 | 0.8 | 1.5 |
| Sodium Sulfate, water, minors- Balance to: | 100 | 100 | 100 |

Note 1: One or more of: Sokolan PA30 ®, BASF or Accusol 480N ®, Rohm & Haas.
Note 2: SLF18 ®, Olin Corp. or LF404 ®, BASF.

EXAMPLE XII

The following liquid automatic dishwashing detergent compositions are prepared by mixing:

| Example XII INGREDIENTS | wt % |
| --- | --- |
| Multiquaternary Bleach Activator Compound of any of Examples I–III (wax-encapsulated) | 0.5 |
| Hydrogen Peroxide Source (Sodium perborate monohydrate, wax-encapsulated): | 7 |
| Potassium Hydroxide | 2 |
| Potassium Carbonate | 8 |
| Aluminum Tristearate | 0.1 |
| Potassium Silicate | 5 |
| Sodium Silicate | 1 |
| low foaming nonionic surfactant | 2 |
| Thickener(DOWFAX ®) | 0.5 |
| Sodium Tripolyphosphate | 17.5 |
| Clay | 1 |
| Sodium Benzoate | 1 |
| Water, perfumes, colorants- Balance to: | 100 |

The above examples are, of course, illustrative and are not intended to be limiting of the invention. The invention provides numerous advantages to the consumer, such as excellent removal of tea stains, starchy soil removal, excellent spotlessness and lack of film on both glasses and dishware, excellent silvercare, and economy. The present automatic dishwashing compositions may be formulated into any convenient form, including liquids, pastes or gels, solids such as tablets; low density, noncompact granules; and compact granules of either phosphate-built or nonphosphate built types.

The ADD's of the above dishwashing detergent composition examples are used to wash tea-stained cups, starch-soiled and spaghetti-soiled dishes, milk-soiled glasses, starch, cheese, egg or babyfood-soiled flatware, and tomato-stained plastic spatulas by loading the soiled dishes in a domestic automatic dishwashing appliance and washing using either cold fill, 60° C. peak, or uniformly 45°–50° C. wash cycles with a product concentration of the exemplary compositions of from about 1,000 to about 5,000 ppm, with excellent results.

What is claimed is:

1. An automatic dishwashing detergent composition comprising
   (a) an effective amount of a source of hydrogen peroxide and
   (b) an effective mount of a bleach activator selected from:

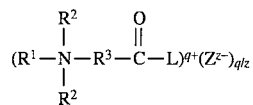

wherein L comprises

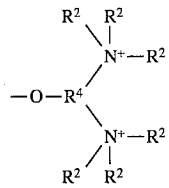

wherein; $R^1$ is $C_1$–$C_{12}$ hydrocarbyl; any $R^2$ is independently selected from $C_1$–$C_4$ alkyl, $C_1$–$C_4$ hydroxyalkyl, and benzyl; $R^3$ is $C_1$–$C_{10}$ hydrocarbyl; $R^4$ is alkylene and $R^2$ on leaving group L is $C_1$–$C_4$ alkyl q is from 3 to 6; and Z is a compatible anion having charge z–.

2. An automatic dishwashing detergent composition according to claim 1 wherein Z is selected from the group consisting of bromide, chloride, phosphates, isethionate, carboxylates, polycarboxylates, methanesulfonate, ethanesulfonate, benzenesulfonate, p-toluenesulfonate, cumenesulfonate, xylenesulfonate, naphthalene sulfonate, methyl sulfate, octyl sulfate, and mixtures thereof.

3. An automatic dishwashing detergent composition according to claim 2 further comprising a water-soluble silicate.

4. An automatic dishwashing detergent composition according to claim 3 further comprising a low-foaming nonionic surfactant.

5. An automatic dishwashing detergent composition according to claim 4 comprising:
   from about 0.1% to about 70% of said source of hydrogen peroxide, (a);
   from about 0.1% to about 30% of said bleach activator, (b);
   from about 0.1% to about 40% of said water-soluble silicate; and
   from about 0.1% to about 20% of said low-foaming nonionic surfactant.

6. An automatic dishwashing detergent composition according to claim 5 comprising:
   from about 0.5% to about 30% of said source of hydrogen peroxide, (a);
   from about 0.1% to about 10% of said bleach activator, (b);
   from about 0.1% to about 20% of said water-soluble silicate; and
   from about 0.1% to about 10% of said low-foaming nonionic surfactant.

7. An automatic dishwashing detergent composition according to claim 4 further comprising from about 0.1% to about 15% of a polymeric dispersant.

8. An automatic dishwashing detergent composition according to claim 7 further comprising from about 0.01% to about 10% of a chelant.

9. An automatic dishwashing detergent composition according to claim 8 further comprising from about 0.0001% to about 10% of a detersive enzyme.

10. An automatic dishwashing detergent composition according to claim 9 in which said hydrogen peroxide source is selected from the group consisting of perborate salts, percarbonate salts and mixtures thereof.

11. An automatic dishwashing detergent composition according to claim 10 further comprising (c) a conventional bleach-improving compound.

12. An automatic dishwashing detergent composition according to claim 11 wherein said conventional bleach-improving compound is selected from the group consisting of:
   conventional bleach activators;
   transition metal beach catalysts;
   diacyl peroxides and
   mixtures thereof.

13. An automatic dishwashing detergent composition according to claim 12 which is substantially free from chlorine bleach.

14. An automatic dishwashing detergent composition according to claim 13 which is substantially free from calcium-precipitatable fatty acids.

15. An automatic dishwashing detergent composition according to claim 14 which is substantially free from phosphorus builders.

16. An automatic dishwashing detergent composition according to claim 15 having compact granular form.

17. An automatic dishwashing detergent composition according to claim 16 wherein said composition has an aqueous pH in the range from about 7 to about 12.

18. A bleach activator compound comprising a cation selected from the group consisting of

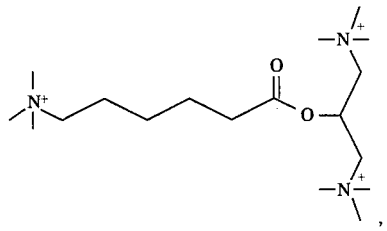
,

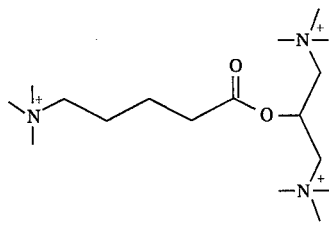

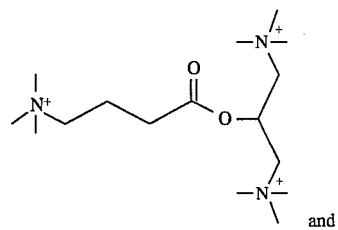
and

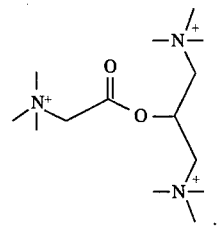
.

19. A bleach activator according to claim 18 consisting essentially of said cation and a charge-balancing amount of compatible anions.

* * * * *